(12) United States Patent
Shay et al.

(10) Patent No.: US 6,210,915 B1
(45) Date of Patent: Apr. 3, 2001

(54) TELOMERASE EXTRACTION METHOD

(75) Inventors: Jerry W. Shay, Dallas; Woodring E. Wright, Arlington, both of TX (US); James C. Norton, Jr., Nashville, TN (US)

(73) Assignee: University of Texas Systems, Austin, TX (US)

( * ) Notice: Subject to any disclaimer, the term of this patent is extended or adjusted under 35 U.S.C. 154(b) by 0 days.

(21) Appl. No.: 09/219,270

(22) Filed: Dec. 23, 1998

Related U.S. Application Data

(60) Provisional application No. 60/070,076, filed on Dec. 31, 1997.

(51) Int. Cl.⁷ .............................. C12Q 1/48; C12Q 1/68; C12N 9/10

(52) U.S. Cl. .................................. 435/15; 435/6; 435/193

(58) Field of Search ................................ 435/6, 15, 91.2, 435/193

(56) References Cited

U.S. PATENT DOCUMENTS

| | | | |
|---|---|---|---|
| 5,489,508 | 2/1996 | West et al. | 435/6 |
| 5,629,154 | 5/1997 | Kim et al. | 435/6 |
| 5,639,613 | 6/1997 | Shay et al. | 435/6 |
| 5,645,986 | 7/1997 | West et al. | 435/6 |
| 5,648,215 | 7/1997 | West et al. | 435/6 |
| 5,693,474 | 12/1997 | Shay et al. | 435/6 |
| 5,695,932 | 12/1997 | West et al. | 435/6 |
| 5,837,453 | 11/1998 | Harley et al. | 435/6 |
| 5,840,490 | 11/1998 | Bacchetti et al. | 435/6 |

FOREIGN PATENT DOCUMENTS

| | | | |
|---|---|---|---|
| WO 93/23572 | 11/1993 | (WO) | C12Q/1/68 |

OTHER PUBLICATIONS

Anonymous, "Enhanced Extraction of Telomerase Activity from Cultured Cells and Tissue Samples (Meeting Abstract)", Proc Annu Meet Am Assoc Cancer Res, vol. 38, p. A3385, in Cancerlit, AN 1998640385, 1997.*

CalBiochem, "A Guide to the Properties and Uses of Detergents in Biology and Biochemistry", Hoechst Celanese Corporation, 1987.*

Allsopp et al., "Telomere Length Predicts Replicative Capacity of Human Fibroblasts," Proc. Natl. Acad. Sci. USA, vol. 89, pp. 10114–10118, 1992.

Blackburn, "Structure and Function of Telomeres," Nature, vol. 350, pp. 569–573, 1991.

Collins et al., "Purification of Tetrahymena Telomerase and Cloning of Genes Encoding the Two Protein Components of the Enzyme," Cell, vol. 81, pp. 677–686, 1995.

Cremo et al., "Solubilization of the Artrial Muscarinic Acetylcholine Receptor: A New Detergent System and Rapid Assays," Anal. Biochem., vol. 115, pp. 331–338, 1981.

De Lange et al., "Structure and Variability of Human Chromosome Ends," Mol. Cell. Biol., vol. 10, No. 2, pp. 518–527, 1990.

Gollahon et al., "Immortalization of Human Mammary Epithelial Cells Transfected with Mutant p53 ($273^{his}$)," Oncogene, vol. 12, pp. 715–725, 1996.

Greider et al., "Identification of a Specific Telomere Terminal Transferase Activity in Tetrahymena Extracts," Cell, vol. 43, pp. 405–413, 1985.

Greider et al., "A Telomeric Sequence in the RNA of Tetrahymena Telomerase Required for Telomere Repeat Synthesis," Nature, vol. 337, pp. 331–337, 1989.

Harley et al., "Telomeres Shorten During Ageing of Human Fibroblasts," Nature, vol. 345, pp. 458–460, 1990.

Hastie et al., "Telomere Reduction in Human Colorectal Carcinoma and with Ageing," Nature, vol. 346, pp. 866–868, 1990.

Holt et al., "Comparison of the Telomeric Repeat Amplification Protocol (TRAP) to the new Trapeze Telomerase Detection Kit," Methods in Cell Science, vol. 18, pp. 237–248, 1996.

Holt et al., "Refining the Telomere–Telomerase Hypothesis of Aging and Cancer," Nature Biotech., vol. 14, pp. 836–839, 1996.

Holt et al., "Regulation of Telomerase Activity in Immortal Cell Lines," Mol. Cell Biol., vol. 16, No. 6, pp. 2932–2939, 1996.

Ignatoski et al., "Lysis Buffer Composition Dramatically Affects Extraction of Phosphotyrosine–Containing Proteins," Biotechniques, vol. 20, pp. 794–796, 1996.

Kim et al., "Specific Association of Human Telomerase Activity with Immortal Cells and Cancer," Science, vol. 266, pp. 2011–2015, 1994.

McClintock, "The Stability of Broken Ends of Chromosomes in Zea Mays," Genetics, vol. 26, No. 2, pp. 234–282, 1941.

Morin, "The Human Telomore Terminal Transferase Enzyme Is a Ribonucleoprotein That Synthesizes TTAGGG Repeats," Cell, vol. 59, pp. 521–529, 1989.

Muller, "The Remaking of Chromosomes," The Collecting Net, vol. 13, No. 8, pp. 181–198, 1938.

(List continued on next page.)

*Primary Examiner*—Jon P. Weber
(74) *Attorney, Agent, or Firm*—Narinder S. Banait; Marcella Lillis

(57) ABSTRACT

A method of extracting telomerase from a cell sample having telomerase is provided which includes the step of contacting a cell sample with a buffer having (i) a non-ionic detergent at a concentration of not more than 5% (v/v) and (ii) an ionic detergent at a concentration of not more than 1 mM, to form a cell lysate. The method provides efficient extraction of telomerase that can be assayed for diagnostic and prognostic purposes.

15 Claims, 1 Drawing Sheet

OTHER PUBLICATIONS

Norton et al., "Enhanced Detection of Human Telomerase Activity," DNA and Cell Biology, vol. 17, No. 3, pp. 217–219, 1998.

Piatyszek et al., "Detection of Telomerase Activity in Human Cells and Tumors by a Telomeric Repeat Amplification Protocol (TRAP)," Methods in Cell Science, vol. 17, pp. 1–15, 1995.

Shay et al., "A Survey of Telomerase in Human Cancer," European Journal of Cancer, vol. 33, No. 5, pp. 787–791, 1997.

Vaziri et al., "Loss of Telomeric DNA during Aging of Normal and Trisomy 21 Human Lymphocytes," Amer. J. Hum. Genet., vol. 52, pp. 661–667, 1993.

* cited by examiner

TELOMERASE EXTRACTION METHOD

This application claims priority under 35 U.S.C. 119(e) to application Ser. No. 60/070,076, filed Dec. 31, 1997.

This invention was supported in part by a grant from the National Cancer Institute (F32-CA67477). The U.S. Government may have rights in this invention.

TECHNICAL FIELD

The present invention relates to telomerase, a ribonucleoprotein enzyme involved in telomere DNA synthesis, and provides protocols for extracting telomerase from cell samples and assaying the extracted telomerase. The invention provides methods and compositions relating to the fields of molecular biology, and medical diagnostic and prognostic technologies.

BACKGROUND

Telomeres are genetic elements located at the ends of all eukaryotic chromosomes which preserve genome stability and cell viability by preventing aberrant recombination and degradation of DNA (McClintock, 1941; Muller, 1938). In humans, the telomeric sequence is composed of 10–20 kilobases of TTAGGG repeats (Blackburn, 1991; de Lange et al., 1990). There is increasing evidence that gradual loss of telomeric repeat sequences may be a timing ("clock") mechanism limiting the number of cellular divisions in normal cells (Allsopp et al., 1992; Harley et al., 1990; Hastie et al., 1990; Vaziri et al., 1993). In contrast, immortal cells are capable of maintaining a stable telomere length by upregulating or reactivating telomerase, a ribonucleoprotein enzyme that is able to add TTAGGG repeats to the ends of chromosomes (Greider and Blackburn, 1985; Greider and Blackburn, 1989; Morin, 1989).

Methods for detecting telomerase activity, as well as for identifying compounds that regulate or affect telomerase activity, together with methods for therapy or diagnosis of cellular senescence and immortalization by controlling or measuring telomere length and telomerase activity, have been described. See PCT patent publication No. 93/23572, U.S. Pat. Nos. 5,629,154, 5,648,215, 5,645,986, 5,695,932 and 5,489,508. Each of the foregoing patent publications are incorporated herein by reference.

For example, U.S. Pat. Nos. 5,629,154 and 5,648,215 describe in detail the preparation of a cell extract using a detergent lysis method and the analysis of telomerase activity by the Telomeric Repeat Amplification Protocol (TRAP assay). The telomerase activity assays described therein involve the extension of a nucleic acid substrate by telomerase and replication of extended substrates in a primer extension reaction, such as the polymerase chain reaction (PCR).

Other telomerase extraction methods use hypotonic swelling and physical disruption of cells and telomerase activity is assayed using an oligonucleotide substrate, a radioactive deoxyribonucleoside triphosphate (dNTP) for labelling any telomerase-extended substrate, and gel electrophoresis for resolution and display of products (Morin, 1989). Because telomerase stalls and can release the DNA after adding the first G in the 5'-TTAGGG-3' telomeric repeat, the characteristic pattern of products on the gel is a six nucleotide ladder of extended oligonucleotide substrates. The phase of the repeats depends on the 3'-end sequence of the substrate; telomerase recognizes where the end is in the repeat and synthesizes accordingly to yield contiguous repeat sequences.

Using the TRAP assay, telomerase activity has been detected in 85% of primary human tumors tested from a variety of tissue types (Kim et al., 1994; Shay and Bacchetti, 1997). The detection of telomerase activity in human cells almost always correlates with indefinite proliferation capability (immortalization). U.S. Pat. No. 5,648,215 describes the presence of telomerase activity in somatic cells as indicative of the presence of immortal cells, such as certain types of cancer cells, which can be used to make that determination even when the cells would be classified as non-cancerous by pathology.

While most published reports to date only indicate that telomerase activity is present or absent, methods for cancer prognosis based upon detecting telomerase activity levels have also been described. See U.S. Pat. Nos. 5,639,613 and 5,693,474, and U.S. application Ser. No. 08/485,454 entitled "Telomerase Activity Associated with Hematological and Colorectal Malignancies" filed Jun. 7, 1995.

It has become increasingly evident that accurately quantitating telomerase activity levels in cell samples would be useful in the elucidation of the biological mechanisms by which telomerase acts, as well as for patient diagnosis and prognosis based on telomerase activity levels. Although useful information has been obtained from telomerase assays using the detergent based extraction procedure described above, this invention provides an improved telomerase extraction procedure that allows a more accurate determination of telomerase activity levels in a cell sample.

Relevant Literature

Allsopp, R. C., Vaziri, H., Patterson, C., Goldstein, S., Younglai, E. V., Futcher, A. B., Greider, C. W., and Harley, C. B. (1992). Telomere length predicts replicative capacity of human fibroblasts. PNAS 89, 10114–10118.

Blackburn, E. H. (1991). Structure and function of telomeres. Nature 350, 569–573.

Cremo, C. R., Herron, G. S., and Schimerlik, M. I. (1981). Solubilization of the atrial muscarinic acetylcholine receptor: a new detergent system and rapid assays. Anal. Biochem. 115, 331–338.

de Lange, T., Shiue, L., Myers, R. M., Cox, D. R., Naylor, S. L., Killery, A. M., and Varmus, H. E. (1990). Structure and variability of human chromosome ends. Mol. Cell. Biol. 10, 518–526.

Gollahon, L. S., and Shay, J. W. (1996). Immortalization of human mammary epithelial cells transfected with mutant p53 (273his). Oncogene 12, 715–725.

Greider, C. W., and Blackburn, E. H. (1985). Identification of a specific telomere terminal transferase activity in Tetrahymena extracts. Cell 43, 405–413.

Greider, C. W., and Blackburn, E. H. (1989). A telomeric sequence in the RNA of Tetrahymena telomerase required for telomere repeat synthesis. Nature 337, 331–337.

Harley, C. B., Fletcher, A. B., and Greider, C. W. (1990). Telomeres shorten during aging. Nature 345, 458–460.

Hastie, N. D., Dempster, M., Dunlop, M. G., Thompson, A. M., Green, D. K., and Allshire, R. C. (1990). Telomere reduction in human colorectal carcinoma and with ageing. Nature 346, 866–868.

Holt, S. E., Norton, J. C., Wright, W. E., and Shay, J. W. (1996). Comparison of the telomeric repeat amplification protocol (TRAP) to the new TRAP-eze telomerase detection kit. Methods in Cell Science 18, 237–248.

Holt, S. E., Shay, J. W., and Wright, W. E. (1996). Refining the telomere-telomerase hypothesis of aging and cancer. Nature Biotech. 14, 836–839.

Holt, S. E., Wright, W. E., and Shay, J. W. (1996). Regulation of telomerase activity in immortal cell lines. Mol. Cell. Biol. 16, 2932–2939.

Ignatoski, K. M., and Verderame, M. F. (1996). Lysis buffer composition dramatically affects extraction of phosphotyrosine-containing proteins. Biotechniques 20, 794–6.

Kim, N. W., Piatyszek, M. A., Prowse, K. R., Harley, C. B., West, M. D., Ho, P. L., Coviello, G. M., Wright, W. E., Weinrich, S. L., and Shay, J. W. (1994). Specific association of human telomerase activity with immortal cells and cancer. Science 266, 2011–2015.

McClintock, B. (1941). The Stability of Broken Ends of Chromosomes in Zea maize. Genetics 26, 234–282.

Morin, G. B. (1989). The human telomere terminal transferase enzyme is a ribonucleoprotein that synthesizes TTAGGG repeats. Cell 59, 521–529.

Muller, H. J. (1938). The Remaking of Chromosomes. The Collecting Net 13, 181–198.

Piatyszek, M. A., Kim, N. W., Weinrich, S. L., Keiko, H., Hiyama, E., Wright, W. E., and Shay, J. W. (1995). Detection of telomerase activity in human cells and tumors by a telomeric repeat amplification protocol (TRAP). Methods in Cell Science 17, 1–15.

Shay, J. W., and Bacchetti, S. (1997). A survey of telomerase activity in human cancer. European Journal of Cancer 5, 787–791.

Vaziri, H., Schachter, F., Uchida, I., Wei, L., Zhu, X., Effros, R., Cohen, D., and Harley, C. B. (1993). Loss of telomeric DNA during aging of normal and trisomy 21 human lymphocytes. Amer. J. Human Genetics 52, 661–667.

SUMMARY OF THE INVENTION

It is an object of the present invention to provide a method for the efficient extraction of telomerase from a cell sample.

It is a further object of the present invention to provide improved detection and quantitation of telomerase activity in a cell sample.

These and other objects of the invention are obtained by providing a method for extracting telomerase from a cell sample using an ionic detergent. In one aspect of the invention, the method comprises:

contacting a cell sample with a buffer comprising (i) a non-ionic detergent at a concentration of not more than 5% (v/v) and (ii) an ionic detergent at a concentration of not more than 1 mM to form a cell lysate.

The cell lysate produced using the telomerase extraction procedure of the present invention can be used to assay telomerase activity. Thus, in a further aspect of the invention, a method for detecting telomerase activity is provided, comprising contacting a cell sample with a buffer comprising a non-ionic detergent at a concentration of not more than 5% (v/v) and an ionic detergent at a concentration of not more than 1 mM to form a cell lysate and incubating the cell lysate with a telomerase substrate under conditions that allow telomerase to catalyze extension of the telomerase substrate by addition of telomeric repeat sequences; and detecting any extended telomerase substrate. The extended telomerase can be detected by a variety of means, including using a polymerase chain reaction. Telomerase activity assays are useful in the diagnosis and prognosis of cancer, as well as in other conditions based on a change in telomerase activity.

BRIEF DESCRIPTION OF THE DRAWINGS

FIG. 1A. depicts TRAP products on a polyacrylamide gel illustrating the effect of sequential extractions of a cell pellet with CHAPS lysis buffer. The 36 base pair internal standard oligonucleotide (ITAS) is indicated by the arrow. A sample containing 100,000 HME32(273)-1 cells (a telomerase positive human mammary epithelial cell line; Gollahon and Shay, 1996) was initially lysed in 200 μL of CHAPS lysis buffer. After pelleting, 160 μL of the lysate was removed. Fresh lysis buffer (160 μL) was then added to the cell sample and the extraction procedure repeated 4 times.

FIG. 1B. depicts quantitation of the TRAP gel shown in FIG. 1A. The ratio of the signal obtained from the entire telomerase ladder compared to that of the internal standard (ITAS) for each lane was quantitated using a PhosphorImager and Molecular Dynamics software. Results are expressed as a percent of the total activity found in all of the extracts.

FIG. 1C. depicts TRAP products on a polyacrylamide gel illustrating the effect of sequential extractions of a cell pellet with NP-40/NaDOC/150 mM NaCl lysis buffer. The 36 base pair internal standard oligonucleotide (ITAS) is indicated by the arrow. A sample of HT1080 cells was extracted three times with the NP40/NaDOC/150 mM NaCl extraction buffer as described in the Examples section below.

FIG. 1D. Quantitation of the TRAP gel in FIG. 1C as described in FIG. 1B.

DESCRIPTION OF SPECIFIC EMBODIMENTS

Figure 1:
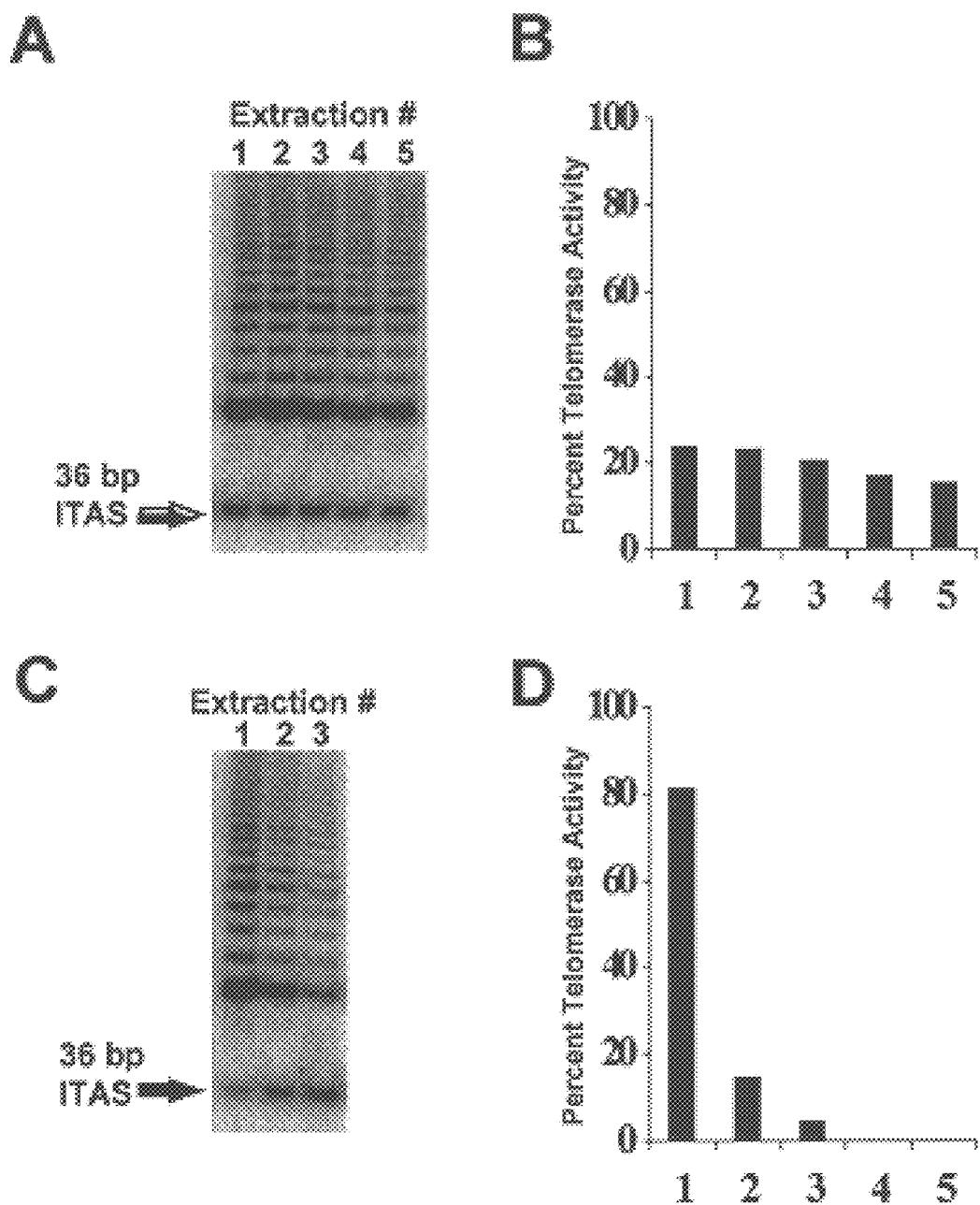
FIG. 1 shows results obtained with the improved telomerase extraction method compared to results obtained with the previously described CHAPS lysis extraction method. Methodology is described in detail in the Examples section below.

The present invention provides methods for extracting telomerase from a cell sample allowing a more accurate determination of the telomerase activity level in a cell sample. As the telomerase activity level in a cell sample has been demonstrated to be a useful indicator of cancer prognosis, it is important to minimize the potential for false telomerase-negative or low telomerase activity samples resulting from inefficient telomerase extraction. Some tumor derived cell lines originally thought to contain differing amounts of telomerase using prior art techniques have been demonstrated to have nearly equivalent amounts of activity when telomerase was extracted using the method of the present invention. The Examples section below provides evidence demonstrating the efficiency of telomerase extraction using the method of the present invention in that nearly all the telomerase in a cell sample can be extracted.

The methods of the present invention involves the extraction of telomerase from a cell or tissue sample, which sample will often be obtained from a human, but one can also readily understand that samples tested by the present method can be obtained from agriculturally important mammals, such as cattle, horses, sheep, etc., or other animals of veterinary interest, such as cats and dogs. The extraction procedure can be carried out on any cell or tissue sample, such as blood, normal somatic tissues, germline tissues, or cancerous tissues. The cell or tissue sample can be obtained by methods known in the art, such as, from biopsies and surgical resections. In addition, the sample can be cells grown in the laboratory, such as cells of an experimentally derived cell line.

In one aspect of the invention, a method is provided for extracting telomerase from a cell sample containing telomerase by contacting the cell sample with a buffer comprising an ionic detergent, optionally in combination with a non-ionic and/or zwitterionic detergent, to form a cell lysate. By "extracting", it is meant that the telomerase is provided in assayable form after disruption of the cell containing the telomerase, thus forming a cell lysate. There is no requirement for any further manipulation of the sample, although in some cases a purification step, such as, the removal of cellular debris from the cell lysate may be desirable. Cellular debris can easily be removed by methods known in the art, such as by centrifugation or filtration.

As stated above, telomerase is extracted from the cell sample by contacting the cell sample with a buffer comprising an ionic detergent or an ionic detergent in combination with a non-ionic and/or zwitterionic detergent. The term "ionic detergent" as used herein does not encompass zwitterionic (amphoteric) detergents. Preferably, telomerase is extracted from the cell sample by using a buffer comprising a combination of a non-ionic and an ionic detergent.

A wide variety of non-ionic, zwitterionic and ionic detergents can be employed in preparing the cell lysate. For example, preferred non-ionic detergents include TWEEN 20, TRITON X-100, TRITON X-114, THESIT, NONIDET NP-40, n-octylglucoside, n-dodecylglucoside, n-dodecyl-beta-D-maltoside, octanoyl -N-methylglucamide (MEGA-8), decanoyl-N-methylglucamide (MEGA-10), and isotridecyl-poly (ethyleneglycolether)$_n$, preferred zwitterionic detergents include CHAPS (3-{(3-cholamidopropyl) dimethylammonio}-1-propane-sulfonate), CHAPSO (3-{(3-cholamidopropyl)dimethyl-ammonio}-2-hydroxy-1-propane-sulfonate), N-dodecyl-N, N-dimethyl-3-ammonio-1-propane-sulfonate, and digitonin, and preferred ionic detergents include sodium or lithium dodecyl sulfate, sodium deoxycholate, and sodium glycocholate. Particularly preferred detergents are sodium dodecylsulfate, sodium deoxycholate, octylphenol-polyethylene glycol ether (TRITON X-100), Tergitol (NONIDET NP-40) and polyoxyethylenesorbitan monolaurate (TWEEN-20).

While the exact amount of detergent is not critical, care is taken to avoid denaturation of the telomerase through the addition of excessive amounts of detergent. Typically, a concentration of not more than 5% (v/v), preferably not more than 2% (v/v), more preferably not more than 1% (v/v) of the non-ionic and/or zwitterionic detergent is used. Ionic detergent is used in the buffer at a concentration of not more than 1 mM, preferably not more than 0.5 mM, more preferably not more than 0.25 mM to prepare the cell lysate. A preferred buffer provides a combination of detergents, having a non-ionic detergent at a concentration of not more than 5% (v/v) and an ionic detergent at a concentration of not more than 1 mM. In any event, sufficient detergent is used to ensure cell lysis and telomerase extraction, and the amount can be determined using the telomerase activity assays described below. Non-ionic detergent at a concentration of 1% and ionic detergent at a concentration of 0.25 mM is sufficient to observe enhanced extraction of telomerase activity, although numerous other combinations can also be used in the method of the present invention, as is evident to one of ordinary skill in the art.

The cell lysis buffer will often contain components other than detergent. For example, polyhydroxylated compounds (e.g., glycerol), protease inhibitors (phenylmethylsulfonyl fluoride, PMSF; 4-(2-aminoethyl)-benzenesulfonyl fluoride hydrochloride,AEBSF; pepstatin A), ion chelators (EDTA, EGTA), dithiothreitol (DTT), β-mercaptoethanol or other stabilizing agents may be included, together with buffer ions (Tris, Hepes) and salts (magnesium chloride, sodium chloride, potassium chloride, phosphate). Buffer components useful in extracting proteins are described in Scopes, *Protein Purification: Principles and Practice,* Second Edition (Springer-Verlag, N.Y., 1987). A particularly preferred cell lysis buffer comprises a salt, such as sodium chloride or potassium chloride, at a physiologically acceptable concentration, such as at a concentration of about 150 mM.

In the method of the invention, the cell sample will be in contact with the buffer for a sufficient period of time to allow cell lysis and extraction of telomerase. Typically, the extract will be incubated for 10–60 minutes.

Consistency in the telomerase extraction procedure can be ensured by using a variety of techniques. For example, to control for the quality of each tissue extract, another enzymatic activity normally associated with the cell sample, such as alkaline phosphatase, can serve as an internal control.

The telomerase provided by the extraction procedures of the present invention can be detected by any of a variety of techniques, for example, using antibodies specific for telomerase. Preferably, telomerase activity is measured. If desired (but not required), the telomerase can undergo further manipulations after formation of the cell extract for activity assays. However, these separations are generally difficult and may result in loss of telomerase activity, and thus, because telomerase assays do not require purified telomerase, cell extracts that have not been pretreated are preferred for assay.

In this invention, there are no limitations on the type of assay used to measure telomerase activity. Any of the current assays for telomerase activity can be used, as well as assays that may be developed in the future. U.S. application Ser. Nos. 08/482,132, 08/631,554 and 08/632,662 entitled "Telomerase Activity Assays" filed on Jun. 7, 1995, Apr. 12, 1996 and Apr. 15, 1996, respectively, all describe suitable methods for determining telomerase activity. A particularly preferred method involves the analysis of telomerase activity by the Telomeric Repeat Amplification Protocol (TRAP assay). This method is described in detail in U.S. application Ser. Nos. 08/482,132, 08/631,554 and 08/632,662, as well as in U.S. Pat. Nos. 5,629,154 and 5,648,215.

The TRAP assay is particularly well suited for providing a variety of means to quantitate the amount of telomerase in a sample. One important means for obtaining quantitative information is the use of a control oligonucleotide template added to each reaction mixture in a known amount. An illustrative control oligonucleotide comprises, in 5'–3' order, a telomerase substrate sequence, a spacer sequence (which can be any sequence of nucleotides or length and can alter spacing of the ladder produced by electrophoresis of reaction products produced from telomerase containing samples), a telomeric repeat sequence (typically present in multiple, i.e., 2 to 50, copies), and a sequence complementary to the primer used in the assay (and so which may simply be a portion of the telomeric repeat sequence). Of course, an oligonucleotide complementary to the control sequence defined above can also serve as the control sequence, and a double-stranded control nucleic acid can also be employed.

Alternatively, one can add a control nucleic acid of any sequence to the reaction mixture in known amounts and amplify the control with primers which can be the same as or different from those used to amplify the extended telomerase substrate. The control oligonucleotide and/or the primers used to amplify the control oligonucleotide can be labelled identically to or differently from the label used to detect the telomerase extension products. Use of an internal control not only facilitates the determination of whether the assay was conducted properly but also facilitates quantitation of the telomerase activity present in the sample. The detailed protocol for conducting TRAP assays using primer and internal control is described in U.S. Pat. No 5,629,154.

Normalizing the intensity of the telomerase ladder to that of the internal standard permits the assay to become linear so that accurate comparisons between samples can be made, as is described in the Examples section below. A weak signal resulting from the internal standard relative to that in other samples could indicate limiting PCR conditions, thus allowing the practitioner to choose to repeat the assay under non-limiting conditions, for example, by providing higher polymerase levels. The inclusion of the internal standard also immediately identifies potentially false negative tumor samples that contain, e.g., Taq polymerase (commonly used in PCR) inhibitors.

While PCR provides for exponential accumulation of primer extension products, even linear accumulation of primer extension products can provide useful results. Thus, one can use a single primer and merely make many copies of a single strand of the duplex nucleic acid that is produced when PCR is employed. Moreover, such copies can be made by means other than polymerase-mediated primer extension. Suitable methods include the ligase chain reaction (Barany, 1991, *Proc. Natl. Acad. Sci. USA* 88:189–193), nucleic acid sequence-based amplification (Compton, 1991, *Nature* 350:91–92), self-sustained sequence replication (Guatelli et al., 1990, *Proc. Natl. Acad. Sci. USA* 87:1874–1878), strand displacement amplification (Walker et al., 1992, *Proc. Natl. Acad. Sci. USA* 89:392–396), and branched DNA signal amplification (Urdea, Sept. 12, 1994, *Bio/Tech.* 12:926–928; U.S. Pat. No. 5,124,246), although the latter method involves amplification of the signal produced upon probe hybridization to a target nucleic acid.

Moreover, a variety of different types of oligonucleotides can be used in telomerase activity assays. While the discussion above and Examples below illustrate assay methods with results obtained using oligodeoxyribonucleotide telomerase substrates and primers with DNA polymerase, the activity assay used in the present invention is not so limited. Thus, one can employ oligoribonucleotides or oligonucleotides that comprise one or more modified (i.e., synthetic or non-naturally occurring) nucleotides in the telomerase assay. In similar fashion, one can employ an RNA polymerase to extend a primer or to copy an extended telomerase substrate. These and other variations of the present method will be apparent to those of skill in the art upon consideration of this description of the invention.

The telomerase extraction procedure provided herein can be used in any of a variety of applications in conjunction with a telomerase activity assay. For example, U.S. Pat. No. 5,629,154 describes the application of telomerase activity assays to (i) detection of immortal cells in tumor biopsies for the identification of potential cancer cells; (ii) identification of agents capable of activating, derepressing, inhibiting, or repressing telomerase, (iii) identification of stem cells or early progenitor cells that possess telomerase activity, (iv) examination of telomerase regulation during differentiation and development, (v) identification of telomerase during purification, (vi) identification of protozoal and fungal infections, and (vii) diagnosis of certain types of infertility characterized by the absence of telomerase activity. U.S. Pat. No. 5,695,932 describes telomerase activity assays for diagnosing pathogenic infections. U.S. Pat. Nos. 5,639,613 and 5,693,474, as well as U.S. application Ser. No. 08/485,454 entitled "Telomerase Activity Associated with Hematological and Colorectal Malignancies" filed Jun. 7, 1995 describe the application of telomerase activity assays to cancer prognosis. As noted above, the method of the present invention is particularly useful where the accurate determination of the level of telomerase activity in a cell sample is needed.

The present invention also provides kits for performing the methods of the invention. Such kits can be prepared from readily available materials and reagents and can come in a variety of embodiments. For example, such kits can comprise any one or more of the following materials: reaction tubes, buffers, detergent, oligonucleotide telomerase substrates, control reagents, oligonucleotide primers, and instructions. A wide variety of kits and components can be prepared according to the present invention, depending upon the intended user of the kit and the particular needs of the user.

The following examples describe specific aspects of the invention to illustrate the invention and provide a description of the methods for those of skill in the art. The examples should not be construed as limiting the invention, as the examples merely provide specific methodology useful in understanding and practice of the invention.

EXAMPLES

A series of detergents were tested to evaluate efficiency in telomerase extraction from a cell sample. A number of non-ionic and ionic detergents were tested for their ability to prepare a cell extract comprising active telomerase. As a result of these tests, ionic detergents were shown to denature most proteins at concentrations above 1 mM, whereas non-ionic detergents appeared to have no denaturing effects up to a concentration of 5%. A combination of NP-40 and sodium deoxycholate (NaDOC) was found to be the most efficient for extracting telomerase activity.

Methods

Cells were prepared for TRAP assays as described (Kim et al., 1994; Piatyszek et al., 1995) and analyzed using the TRAP-eze™ kit (Holt et al., 1996). The telomerase positive cell lines analyzed were an in vitro immortalized human mammary epthelial cell line (HME32(273)-1) (Gollahon and Shay, 1996) and a human fibrosarcoma line (HT1080). Cells were lysed as previously described (Kim et al., 1994; Piatyszek et al., 1995) with 200 $\mu$L of either a CHAPS lysis buffer (Kim et al., 1994; Piatyszek et al., 1995; Oncor, Inc., Gaithersburg, Md.) or a modified lysis buffer: 10 mM Tris-HCl, pH 7.5, 1 mM MgCl$_2$, 1 mM EGTA, 1% NP-40, 0.25 mM sodium deoxycholate (NaDOC), 150 mM NaCl, 10% glycerol, 5 mM $\beta$-mercaptoethanol, and 0.1 mM AEBSF (4-(2-aminoethyl)-benzenesulfonyl fluoride hydrochloride).

After centrifugation, 160 $\mu$L of the lysate was removed and saved, and 160 $\mu$L of fresh lysis buffer was added to the remaining 40 $\mu$L for re-extraction of the cell sample, followed by a 30 minute incubation on ice and centrifugation. Thus, this procedure carries over 20% of the first extraction into the second. The re-extraction was repeated 2–4 times.

The extracts were subjected to the telomeric repeat amplification protocol (TRAP assay) (Kim et al., 1994; Piatyszek et al., 1995) using the TRAP-eze™ telomerase detection kit (Oncor, Inc., Gaithersburg, Md.) (Holt et al., 1996). Relative amounts of telomerase products were quantitated using ImageQuant (ver. 3.3) software by evaluating each sample lane separately as described previously (Holt et al., 1996).

Results

The efficiency of recovering telomerase activity using the previously described CHAPS lysis buffer (Kim et al., 1994;

Piatyszek et al., 1995) was examined by performing five sequential extractions of HME32(273)-1 cells (FIGS. 1 A & B). The amount of telomerase activity extracted was similar for each extraction with a slight decrease by the fourth and fifth extractions. Since the activity present in four re-extractions using the CHAPS lysis buffer was nearly identical, the detected activity cannot solely be explained as carryover from the previous extraction. Increasing amounts of CHAPS detergent were also tested with no enhanced extraction detected.

Both ionic (sodium dodecylsulfate (SDS) and sodium deoxycholate (NaDOC)) and non-ionic (Triton X-100, NP-40, and Tween-20) detergents were tested for their ability to extract telomerase activity. The ionic detergents appeared to denature most proteins at concentrations above 1 mM, whereas the non-ionic detergents appeared to have no denaturing effects up to a concentration of 5%. A combination of 0.25 mM sodium deoxycholate and 1% NP-40 in the lysis buffer proved to be the most effective detergent lysis conditions.

Telomerase may be associated with DNA or other proteins, thus ionic conditions may influence the recovery of telomerase activity from cellular extracts. A salt gradient experiment was performed to determine if increased amounts of telomerase activity could be extracted in the presence of salt. Both sodium chloride (NaCl) and potassium chloride (KCl) were tested by varying the concentration up to 1.0 M in the NP-40/NaDOC lysis buffer.

When the salt was combined with the NP-40/NaDOC lysis buffer, optimal extraction occurred at 150 mM NaCl. The composition of the lysis buffer was 0.25 mM sodium deoxycholate, 1% NP-40, 150 mM NaCl, 10 mM Tris-HCl, pH 7.5, 1 mM $MgCl_2$, 1 mM EGTA, 10% glycerol, 5 mM β-mercaptoethanol, and 0.1 mM AEBSF (4-(2-aminoethyl)-benzenesulfonyl fluoride hydrochloride), referred to as the NP-40/NaDOC/150 mM NaCl lysis buffer. Three- to four-fold more telomerase was extracted with the NP-40/NaDOC/150 mM NaCl lysis buffer from HT1080 cells in the initial extraction when compared to the CHAPS lysis buffer, based on telomerase activity assays. Less than 5% of the detectable telomerase activity remained by the third extraction using the NP-40/NaDOC/150 mM NaCl lysis buffer (FIGS. 1C & D). This suggests that the activity remaining was likely due to a carryover dilution effect upon re-extraction. In other experiments when all remaining lysis buffer was removed after the first extraction (i.e., instead of just 160 μl), little to no telomerase activity was detected after re-extraction.

The linearity of the telomerase signal versus an internal standard was also determined. The relationship was linear from 10 to 4000 cells, similar to that previously described for the TRAP-eze™ kit (Holt et al., 1996).

Four other telomerase-positive cell lines (IDH4, H1299, SW391, and HME50-5) were also tested to determine whether enhanced extraction using NP-40/NaDOC was generally applicable. As with HT1080 cells, these telomerase-positive cell lines showed up to a 4-fold increase in telomerase activity in the initial extraction with only low levels of telomerase activity present in the second extraction.

Using these improved telomerase extraction procedures, some tumor derived cell lines originally thought to contain differing amounts of telomerase using the CHAPS based extraction procedure, are demonstrated to have nearly equivalent amounts of activity when extracted with the NP-40/NaDOC/150 mM NaCl lysis buffer. These results indicate that the improved lysis conditions can be used to extract telomerase activity more efficiently from cell samples, such as tumor-derived cell lines.

The present inventors have shown that while the TRAP assay can be routinely used to detect telomerase activity, by using the improved lysis conditions described herein, more consistent telomerase activity extraction can be obtained after a single extraction from a cell sample, allowing more accurate determination of quantitative levels of telomerase activity.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of extracting telomerase from a cell sample comprising telomerase, said method comprising:
   contacting said cell sample with a buffer comprising (i) a non-ionic detergent at a concentration of not more than 5% (v/v) and (ii) an ionic detergent at a concentration of not more than 1 mM to form a cell lysate wherein the ionic detergent is not zwitterionic.

2. The method of claim 1, further comprising removing cellular debris from said cell lysate.

3. The method of claim 2, wherein said cellular debris is removed by centrifugation.

4. The method of claim 1, wherein said non-ionic detergent is present at a concentration of not more than 2% (v/v).

5. The method of claim 1, wherein said non-ionic detergent is present at a concentration of not more than 1% (v/v).

6. The method of claim 1, wherein said ionic detergent is present at a concentration of not more than 0.5 mM.

7. The method of claim 1, wherein said ionic detergent is present at a concentration of not more than 0.25 mM.

8. The method of claim 1, wherein said ionic detergent is present at a concentration of not more than 0.25 mM and wherein said non-ionic detergent is present at a concentration of not more than 1% (v/v).

9. The method of claim 1, wherein said ionic detergent is selected from the group consisting of sodium dodecylsulfate and sodium deoxycholate.

10. The method of claim 1, wherein said non-ionic detergent is selected from the group consisting of octylphenol-polyethylene glycol ether, Tergitol and polyoxyethylenesorbitan monolaurate.

11. The method of claim 1, wherein said buffer further comprises a salt selected from the group consisting of sodium chloride and potassium chloride.

12. The method of claim 11, wherein said salt is present at a concentration of about 150 mM.

13. A method for detecting telomerase activity, said method comprising:

contacting a cell sample with a buffer comprising (i) a non-ionic detergent at a concentration of not more than 5% (v/v) and (ii) an ionic detergent at a concentration of not more than 1 mM to form a cell lysate wherein the ionic detergent is not zwitterionic;

incubating said cell lysate with a telomerase substrate under conditions that allow telomerase to catalyze extension of said telomerase substrate by addition of telomeric repeat sequences; and detecting any extended telomerase substrate.

14. The method of claim 13, wherein said extended telomerase substrate is detected using a polymerase chain reaction.

15. A composition comprising:

a buffer comprising a non-ionic detergent at a concentration of not more than 5% (v/v) and an ionic detergent at a concentration of not more than 1 mM wherein the ionic detergent is not zwitterionic and telomerase.

* * * * *